(12) United States Patent
Chung

(10) Patent No.: US 8,623,063 B2
(45) Date of Patent: Jan. 7, 2014

(54) MEDICAL TREATMENT APPARATUS USING LASER BEAMS

(75) Inventor: Soung Don Chung, Valencia, CA (US)

(73) Assignee: Soung-Don Chung, Valencia, CA (US)

( * ) Notice: Subject to any disclaimer, the term of this patent is extended or adjusted under 35 U.S.C. 154(b) by 80 days.

(21) Appl. No.: 13/179,114

(22) Filed: Jul. 8, 2011

(65) Prior Publication Data

US 2013/0013029 A1 Jan. 10, 2013

(51) Int. Cl.
*A61N 5/067* (2006.01)

(52) U.S. Cl.
USPC .............................................. 607/89; 607/88

(58) Field of Classification Search
USPC ..................................... 607/88–90
See application file for complete search history.

(56) References Cited

U.S. PATENT DOCUMENTS

| | | | | |
|---|---|---|---|---|
| 3,990,300 | A * | 11/1976 | Kossoff | 73/640 |
| 2001/0007078 | A1* | 7/2001 | Yayama | 607/89 |
| 2010/0028558 | A1* | 2/2010 | Ozawa et al. | 427/558 |

FOREIGN PATENT DOCUMENTS

| | | |
|---|---|---|
| JP | 11-276606 | 10/1999 |
| JP | 2001-187157 | 7/2001 |
| JP | 2004-329474 | 11/2004 |
| KR | 20-0407524 | 1/2006 |
| KR | 10-2009-0117544 | 11/2009 |

* cited by examiner

*Primary Examiner* — Bill Thomson
*Assistant Examiner* — Jeffrey Lipitz
(74) *Attorney, Agent, or Firm* — IP & T Group LLP

(57) ABSTRACT

Provided is a medical treatment apparatus using laser beams, which is used for treating arthritis, myositis, chronic pains and so on. A medical treatment apparatus using laser beams includes: a body; a main laser unit irradiating a main laser beam in a direction perpendicular to an area to be treated; a plurality of auxiliary laser units irradiating auxiliary laser beams to form a focus on a central axis of the main laser beam; and an angle adjustment unit adjusting a focal distance by rotating the auxiliary laser units. The medical treatment apparatus using laser beams is capable of easily varying the angle and distance of the focus of irradiated laser beams. In addition, a treatment effect can be enhanced by the laser beams having different intensities, and the absorption rates of the laser beams can be controlled based on the color of light which is separately irradiated onto the skin of an affected area.

8 Claims, 18 Drawing Sheets

Prior Art

[A-A']

MEDICAL TREATMENT APPARATUS USING LASER BEAMS

BACKGROUND OF THE INVENTION

1. Field of the Invention

Exemplary embodiments of the present invention relate to a medical treatment apparatus; and, more particularly, to a medical treatment apparatus using laser beams, which is used for treating arthritis, myositis, chronic pains and so on.

2. Description of Related Art

Diseases such as arthritis and myositis may be treated or relieved by laser beams. Specifically, when laser beams are irradiated onto an affected area, energy is transferred to mitochondria, and cells are smoothly activated and restored. This may speed up metabolism. Furthermore, blood vessels at the laser-beam-irradiated area are expanded, and blood circulation is promoted. Accordingly, the increase of white blood cells is accompanied. As a result, a sterilizing action for the affected area is activated to promote the infection treatment.

As an example of a conventional medical treatment apparatus using laser beams, Korean Patent Laid-open Publication No. 10-2009-0117544 discloses an arthritis treatment apparatus. Referring to FIG. 1, the arthritis treatment apparatus includes a body 10, an ultrasonic generator 20, a plurality of laser diodes 30, and a handle 40. The ultrasonic generator 20 is provided in the body 10 and serves to generate ultrasonic waves toward the center under the body 10. The plurality of laser diodes 30 are installed at even intervals along the outer circumference of a lower portion of the body 10, and emits laser beams at a constant angle toward the inside of the lower portion of the body. The laser beams are focused on one point on the center line of the ultrasonic waves generated from the ultrasonic generator. The handle 40 is provided at one side of the body 10, and includes a switch for switching the operations of the ultrasonic generator and the laser diodes.

The above-described arthritis treatment apparatus is characterized in that an affected area is minutely vibrated by ultrasonic waves to promote the cartilage reconstruction of a joint, and laser beams are simultaneously used to perform the above-described infection treatment.

However, the body 10 should be closely attached to an affected area, in order to normally apply ultrasonic waves to the affected area. Therefore, the arthritis treatment apparatus may cause an additional pain for a patient having a severe arthritis pain. Furthermore, the arthritis treatment apparatus has a structure in which the focus of laser beams is fixed. Therefore, in order to move the focus, the arthritis treatment apparatus should be moved in a state in which the body is closely attached to an affected area as described above. Furthermore, a concave portion 11 of the body 10 from which laser beams and ultrasonic waves are outputted has a hemispheric shape which reflects the joint portions of a human body, in particular, a knee and an elbow. Therefore, the movement of the body is further limited.

Furthermore, since laser beams irradiated from the arthritis treatment apparatus have the same intensity (power), they may have an undesirable effect upon the surroundings of a core area which is to be treated.

SUMMARY OF THE INVENTION

An embodiment of the present invention is directed to a medical treatment apparatus using laser beams, which is capable of easily varying the focus of laser beams by using a main laser element and a plurality of auxiliary laser elements of which the angle may be changed, such that the laser beams are smoothly and effectively irradiated onto an affected area such as a curved joint.

Another embodiment of the present invention is directed to a medical treatment apparatus using laser beams, which sets the intensity of a main laser beam differently from that of auxiliary laser beams such that the penetration depths thereof differ from each other, thereby increasing a treatment effect.

Another embodiment of the present invention is directed to a medical treatment apparatus using laser beams, which is capable of controlling the absorption rate of laser beams by adjusting the color of light irradiated onto the skin of an affected area.

In accordance with an embodiment of the present invention, a medical treatment apparatus using laser beams includes: a body; a main laser unit irradiating a main laser beam in a direction perpendicular to an area to be treated; a plurality of auxiliary laser units irradiating auxiliary laser beams to form a focus on a central axis of the main laser beam; and an angle adjustment unit adjusting a focal distance by rotating the auxiliary laser units.

The auxiliary laser beams may have a lower intensity that the main laser beam. The main laser unit may be positioned in the center of a front surface of the body. The auxiliary laser units may be radially positioned in the front surface with the main laser beam unit set to the center thereof.

The main laser unit may include a main laser element and a condensing lens condensing the main laser beam outputted from the main laser element. The auxiliary laser units may include: four auxiliary laser elements positioned in a radial form, with the main laser element set to the center thereof; and condensing lenses condensing auxiliary laser beams outputted from the auxiliary laser elements.

The medical treatment apparatus may further include a color adjustment unit irradiate a color, which is adjusted by the intensities of red and blue colors, on the skin of the affected area. The color adjustment unit may include at least one pair of red light emitting diode and blue light emitting diode which are positioned on a front surface of the body. The medical treatment apparatus may further include a control unit controlling the main laser unit, the auxiliary laser units, and the angle adjustment unit. The medical treatment apparatus may further include a control unit controlling the color adjustment unit.

DESCRIPTION OF SPECIFIC EMBODIMENTS

Figure 1:
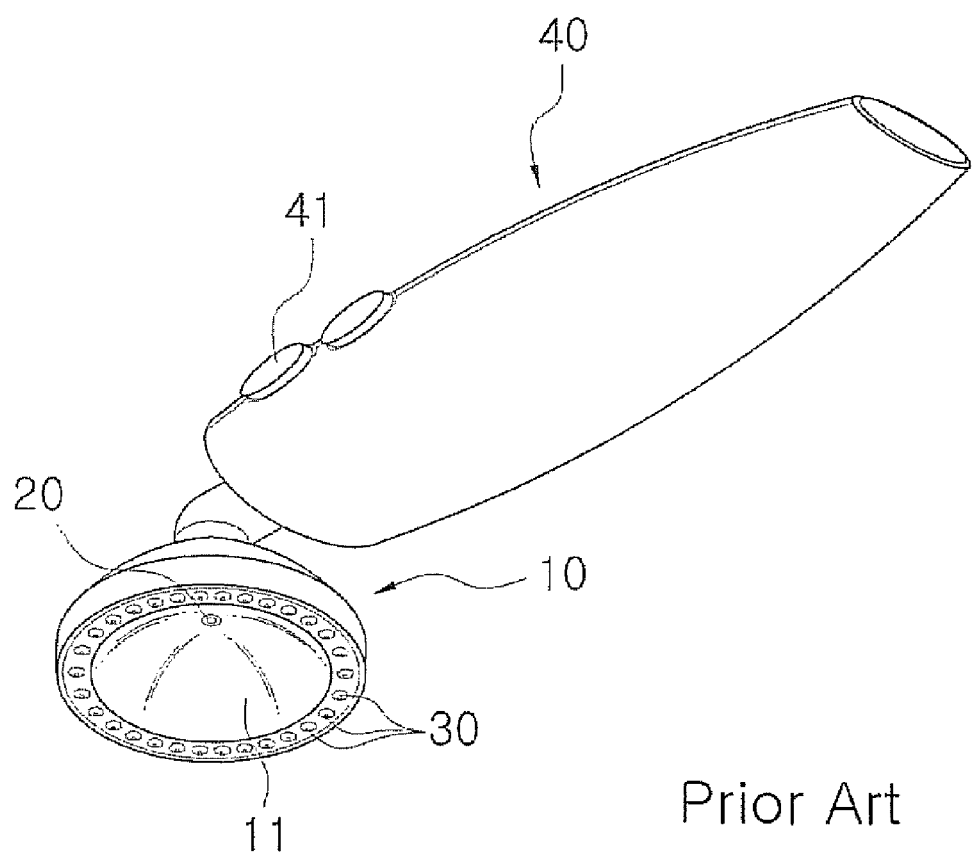
FIG. 1 is a diagram illustrating a conventional medical treatment apparatus using laser beams.

Exemplary embodiments of the present invention will be described below in more detail with reference to the accompanying drawings. The present invention may, however, be embodied in different forms and should not be construed as limited to the embodiments set forth herein. Rather, these embodiments are provided so that this disclosure will be thorough and complete, and will fully convey the scope of the present invention to those skilled in the art. Throughout the disclosure, like reference numerals refer to like parts throughout the various figures and embodiments of the present invention.

Figure 2:
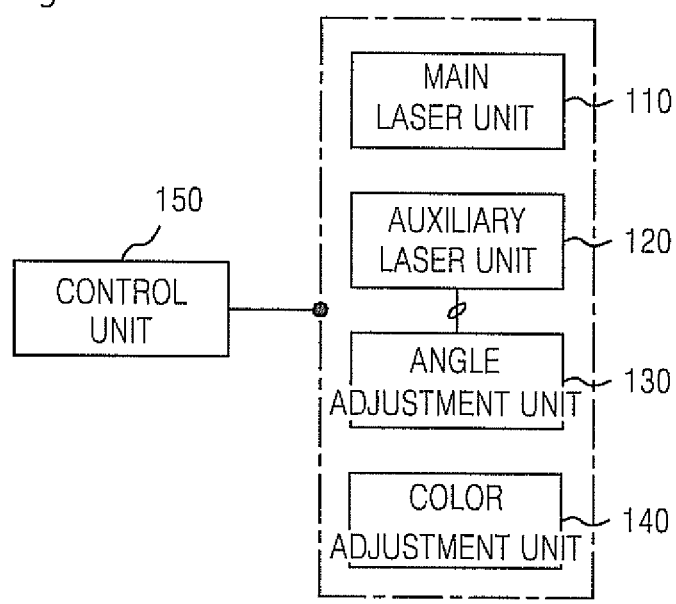
FIG. 2 is a diagram illustrating the functional configuration of a medical treatment apparatus using laser beams in accordance with an embodiment of the present invention.

FIG. 2 is a functional configuration diagram of a medical treatment apparatus using laser beams in accordance with an embodiment of the present invention. The medical treatment apparatus 100 includes a main laser unit 110, a plurality of auxiliary laser units 120, an angle adjustment unit 130, a color adjustment unit 140, and a control unit 150.

Figure 3:
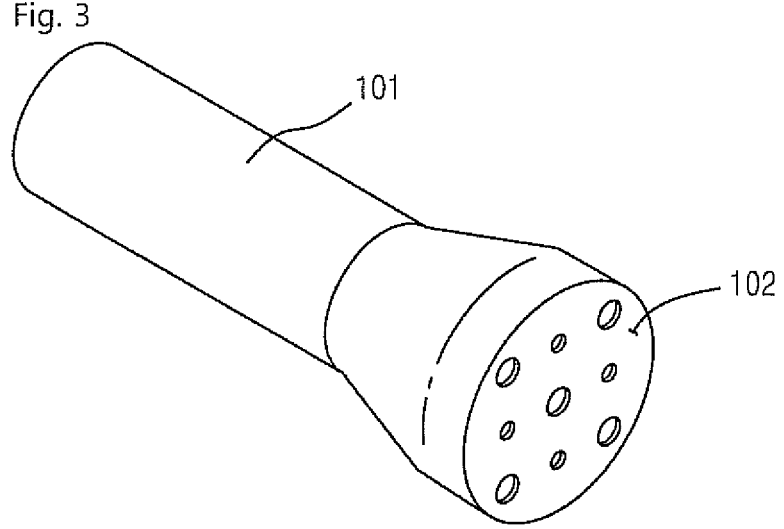
FIGS. 3 and 4 are diagrams explaining a body and a support member in accordance with the embodiment of the present invention.

The main components 110 to 150 for implementing the medical treatment apparatus 100 are provided in a body 101 as illustrated in FIG. 3. The embodiment of the present invention is not limited to the shape or exterior of the body illustrated in the drawing. The control unit 150 may be separated from the body 101. That is, the control unit 150 may be formed in an external type. The shape of the control unit 150 will be described below.

Figure 4:
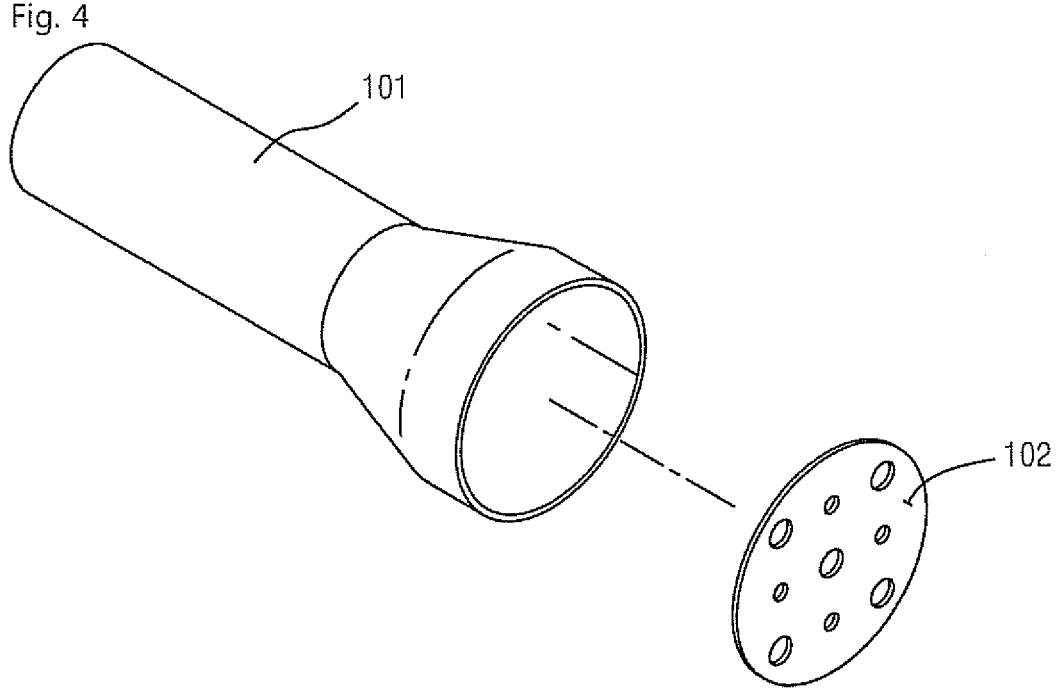

The main laser unit 110, the auxiliary laser units 120, and the color adjustment unit 140 are supported by a support member 102 provided on a front surface of the body 101, from which laser beams are irradiated. In this embodiment of the present invention, the support member 102 is provided as a component integrated with the body 101. As illustrated in FIG. 4, however, the support member 102 may be separated from the body 101. Therefore, the support member 102 described in this embodiment of the present invention may be considered to be the front surface of the body 101.

Figure 5:
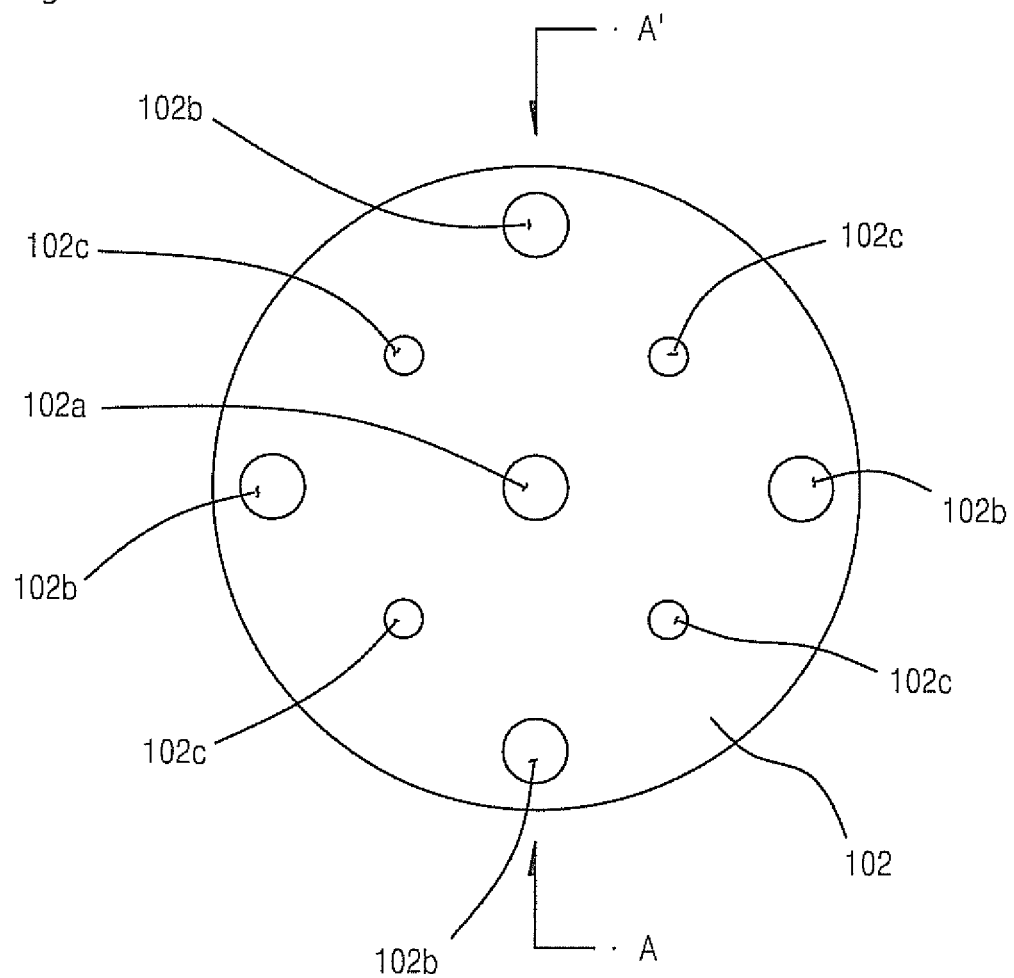
FIG. 5 is a plan view of the support member in accordance with the embodiment of the present invention.
Figure 6:
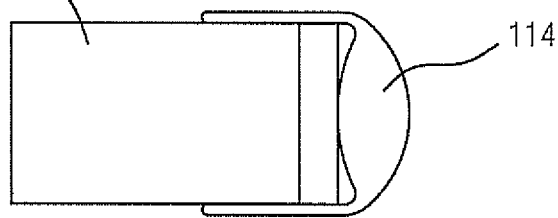
FIG. 6 is a diagram illustrating the detailed structure of a main laser unit in accordance with the embodiment of the present invention.

FIG. 5 is a plan view of the support member 102. The main laser unit 110 is installed in a center hole 102a of the support member 102 and irradiates a laser beam (hereinafter, referred to as a main laser beam for convenience of description) in a direction perpendicular to the front surface. The main laser beam has a wavelength of 880~970 nm and an intensity (power) of 500 mW~5 W. The wavelength and the intensity are controlled by the control unit 150. Referring to FIG. 6, the main laser unit 110 includes a main laser element 112 and a condensing lens 114. The condensing lens 114 serves to increase the power by condensing the main laser beam outputted from the main laser element 112, that is, performs an amplification function.

Figure 7:
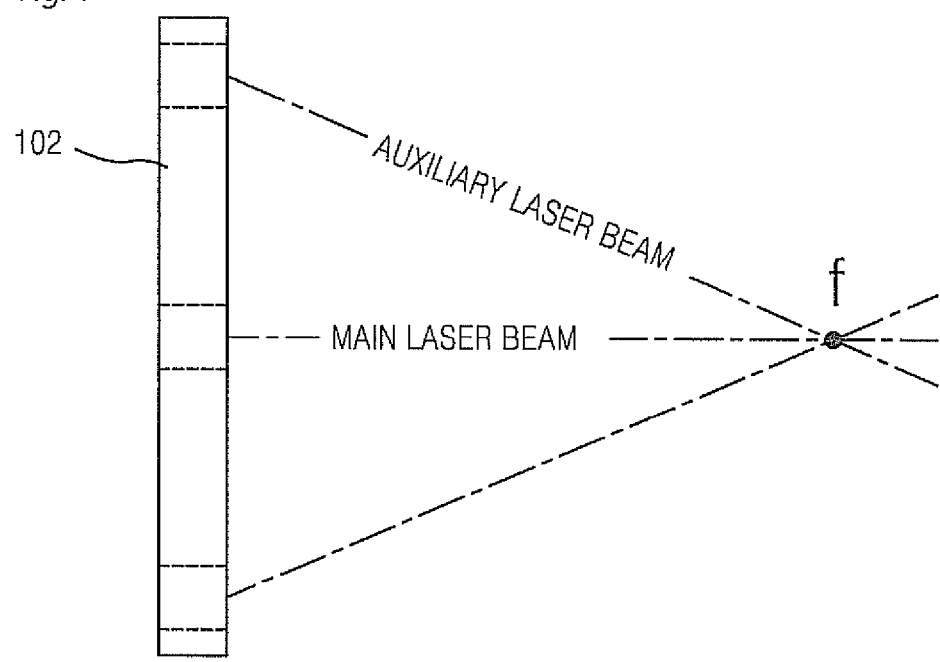
FIG. 7 is a diagram illustrating a focus formed by auxiliary laser units in accordance with the embodiment of the present invention.

Referring to FIG. 5, the auxiliary laser units 120 are installed in auxiliary holes 102 arranged in a radial form, with the main hole 102a set to the center thereof. The auxiliary laser units 120 irradiate auxiliary laser beams toward the main laser beams, the auxiliary laser beams having a wavelength of 750~830 nm and an intensity (power) of 500 mW~1 W. That is, the irradiated auxiliary laser beams form a focus f on a propagation line (hereinafter, referred to as a central axis) of the main laser beam (refer to FIG. 7). At this time, the focal distance (distance from the main laser unit) may be varied by the angle adjustment unit 130 which will be described below.

Figure 8:
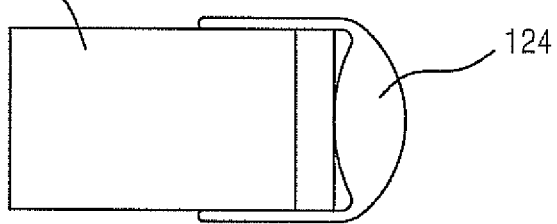
FIG. 8 is a diagram illustrating the detailed structure of the auxiliary laser unit in accordance with the embodiment of the present invention.
Figure 9:
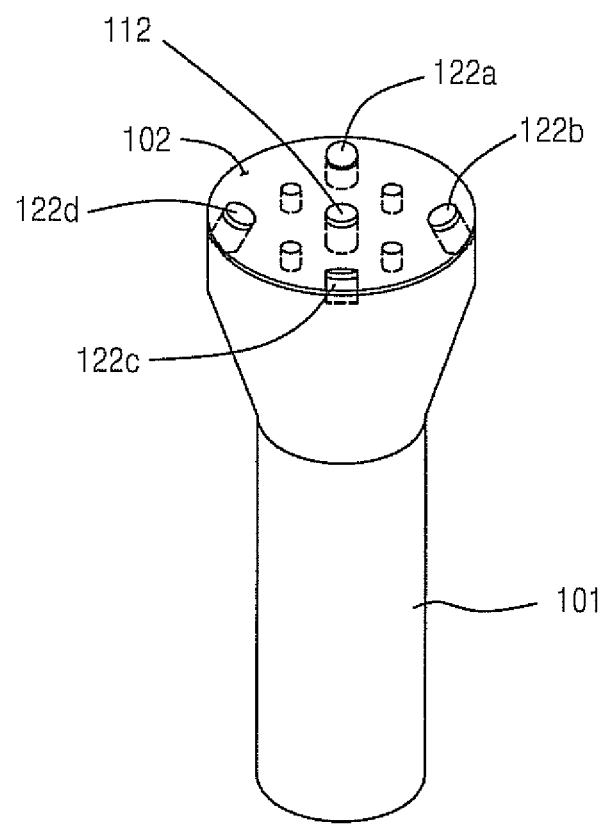
FIG. 9 is a diagram illustrating a main laser unit and auxiliary laser elements positioned in the support member in accordance with the embodiment of the present invention.

Referring to FIG. 8, each of the auxiliary laser units 120 includes an auxiliary laser element 122 and a condensing lens 124, similar to the main laser unit 110. FIG. 9 is a diagram illustrating the main laser element 112 and the auxiliary laser elements 122 which are provided on the support member 102. In this embodiment, the auxiliary laser elements 122a to 122d are installed in four auxiliary holes 102b, respectively. As described above, the auxiliary laser elements 122a to 122d form a focus on the central axis. Here, the variation of the focus means that the auxiliary laser elements 122 are installed in the support member 102 so as to rotate or pivot in a predetermined range.

Figure 10:
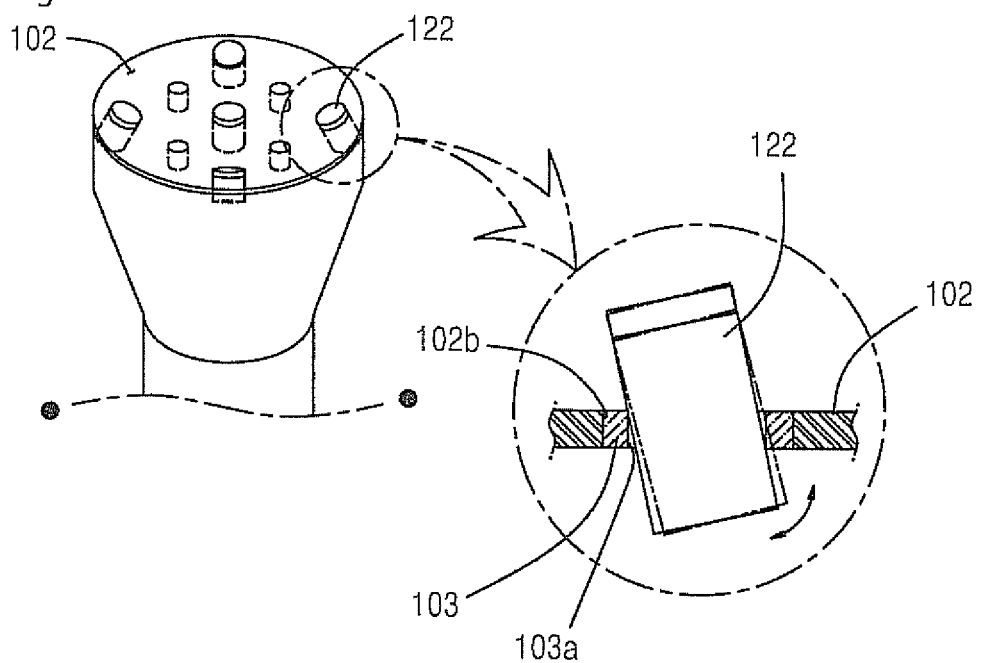
FIG. 10 is a diagram illustrating the rotation of the auxiliary laser element in accordance with the embodiment of the present invention.

Specifically, referring to FIG. 10, a ring-shaped elastic member 103 is provided in the auxiliary hole 102b of the support member 102, which houses the auxiliary laser element 122. The auxiliary laser element 122 is inserted into a hole 103a of the elastic member 103. Therefore, the auxiliary laser element 122 may be rotated in a predetermined range in a state in which the auxiliary laser element 122 is held by the elastic member 103.

Meanwhile, as briefly described above, the angle adjustment unit 130 serves to vary the focal distance by adjusting the angle of the auxiliary laser element 122 with respect to the central axis. The angle adjustment unit 130 may be simply considered to be a unit for rotating the auxiliary laser element. Furthermore, it will be easily understood by those skilled in the art that a specific unit for rotation may be designed and modified in various manners. In this embodiment, however, one example is disclosed as follows.

Figure 11:
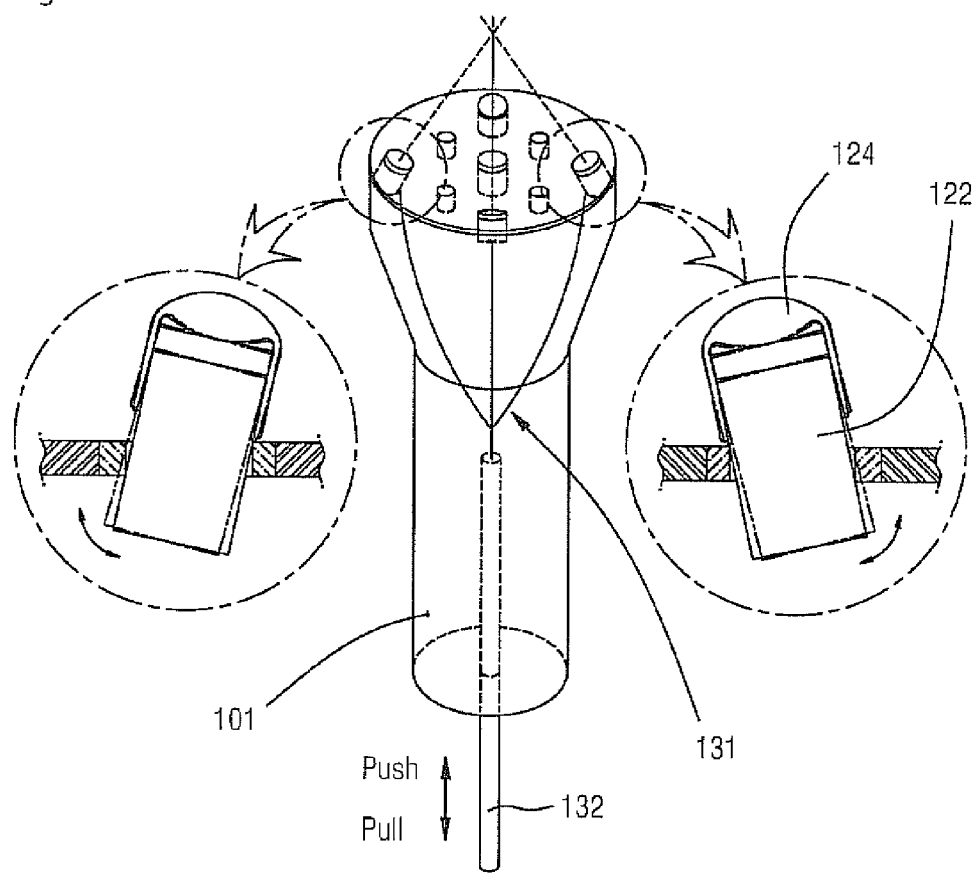
FIG. 11 is a diagram illustrating the detailed structure of an angle adjustment unit in accordance with the embodiment of the present invention.

FIG. 11 is a diagram illustrating the detailed structure of the angle adjustment unit 130 in accordance with the embodiment of the present invention. The auxiliary laser elements 122 are connected to connection members 131, respectively, which are provided under the auxiliary laser elements 122. For example, wires may be used as the connection members 131. Extended ends of the connection members 131 are inserted into the body 101 and connected to a rod 132 which may vertically reciprocate with respect to the support member 102. That is, when the rod 132 is pulled or pushed, the auxiliary laser elements 122 are simultaneously rotated (pivoted) in the same range within the respective auxiliary holes 102b by the movement of the connection members 131. In FIG. 11, when the rod 132 is pushed to the maximum, the focal distance is minimized, and when the rod 132 is pulled to the maximum, the focal distance is maximized.

For reference, the angle adjustment unit 130 of FIG. 11 is based on a manual manipulation method. However, the angle adjustment unit 130 may be implemented according to an automatic manipulation method. For example, gear teeth (not illustrated) may be formed at one side of the rod 132, and a motor-based gear box (not illustrated) for moving the gear teeth may be formed to implement the automatic manipulation method. In this case, the gear box is controlled by the control unit 150. Alternatively, motor-based gear boxes may be installed on the respective auxiliary laser elements 122, in order to individually rotate the auxiliary laser elements 122. As described above, the angle adjustment unit 130 may be implemented in various manners.

Figure 12:
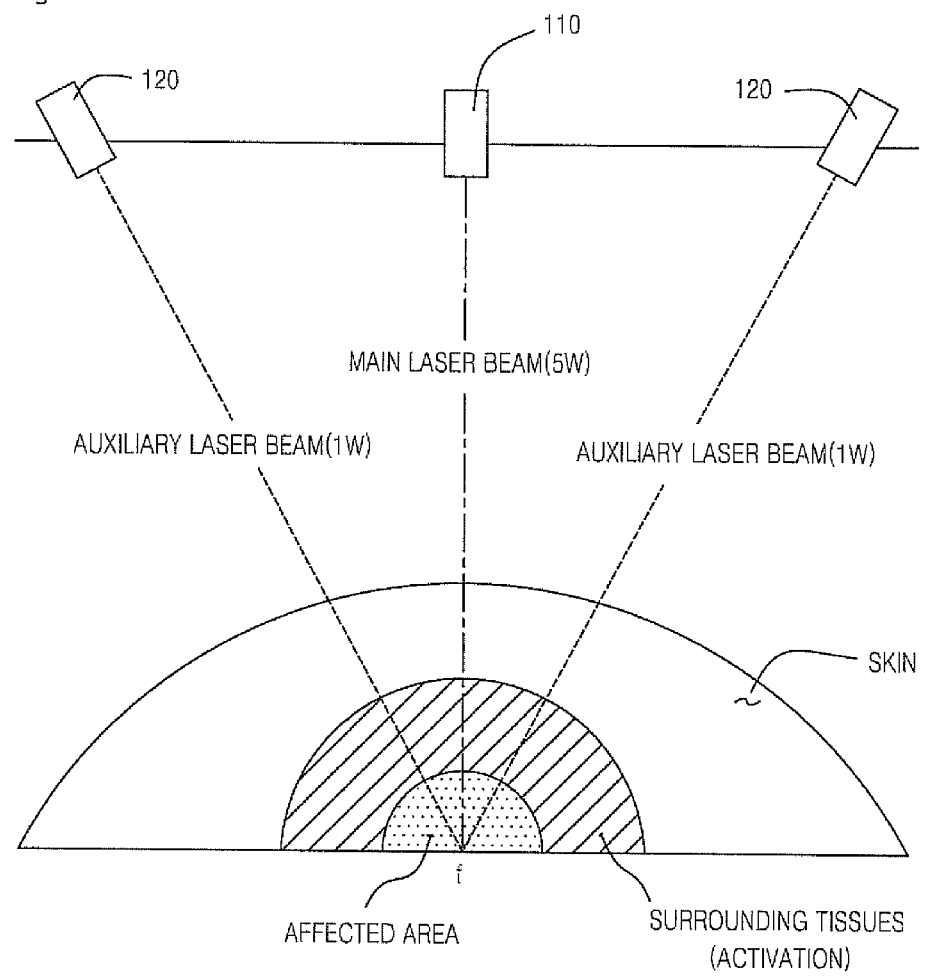
FIGS. 12 and 13 are diagrams illustrating a focus and a focal distance change by the main laser unit and the auxiliary laser units in accordance with the embodiment of the present invention.
Figure 13:
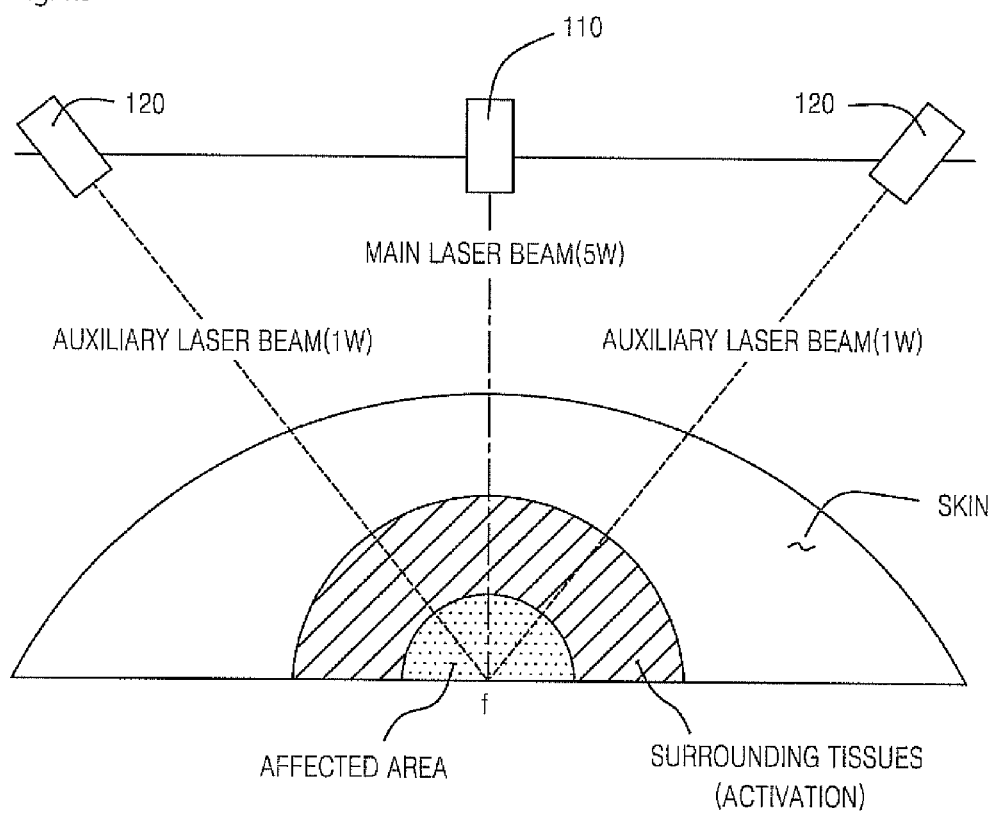

As described above, the intensity (power) of the laser beam outputted from the main laser unit 110 is different from that of the laser beams outputted from the auxiliary laser units 120. The intensity of the main laser beams is set to be higher than that of the auxiliary laser beams. For example, when the intensity of the main laser beam is set to 5 W, the intensity of the auxiliary laser beam may be set to 1 W. When the number of auxiliary laser beams is four as described above, the total intensity at the focus corresponds to 9 W. As well known, the penetration depth of laser beams with respect to a human body may differ depending on the intensity of the laser beams. As the intensity of the laser beams increases, the penetration depth increases. When the intensity of the laser beam outputted from the main laser unit 110 is set to be different from that of the laser beams outputted from the auxiliary laser units 120, it is possible to increase the treatment effect and the stability. This will be specifically described with reference to FIGS. 12 and 13. Although the structure of FIGS. 12 and 13 is illustrated in a two-dimensional manner, the auxiliary laser beams are irradiated onto an affected area in a conical shape, with the main laser beam set to the center thereof. The apex of the conical shape corresponds to the focus f. The auxiliary laser beams serve to activate the surrounding tissues of the affected area before arriving at the affected area. When the surrounding tissues are activated, the metabolism of cells is sped up, and the infection treatment effect at the treated area increases. Furthermore, the auxiliary laser beams having passed through the surrounding tissues converge into the main laser beam (focus f) at the affected area, and the total intensity becomes 9 W. Therefore, a concentrated treatment is performed on the focus area, that is, the affected area. When the focal distance is reduced by the angle adjustment unit 130 as illustrated in FIG. 13, the range of the auxiliary laser beams passing through the surrounding tissues increases. On the other hand, when the focal distance is increased as illustrated in FIG. 12, the range of the auxiliary laser beams passing through the surrounding tissues decreases.

In this embodiment of the present invention, it has been described that the total intensity at the focus area is 9 W, but this is only a numerical value for convenience of description. That is, the loss of laser beams caused by absorption into the human body is excluded. Furthermore, the reason that the intensity of the main laser beam is set to be five times larger than that of the auxiliary laser beams may be described as follows. First, a case in which the intensity of the main laser beam is equal to that of the auxiliary laser beams may be assumed. In this case, when the intensity of each laser beam is set to 5 W, the maximum intensity at the focus area becomes 25 W. This intensity corresponds to such a level that is dangerous to a human body. On the other hand, when the intensity of each beam is reduced to 1 W, the maximum intensity at the focus area becomes 5 W. In this case, although the intensity corresponds to a level safe for a human body, the treatment effect may not be exhibited. In order to set the intensity to 9 W, nine laser elements may be used. However, laser beams having an intensity of 1 W penetrates to a small thickness, and the loss of the laser beams caused by the absorption into a human body increases before the laser beams arrives at the focus area. As a result, the total intensity at the focus area inevitably decreases. That is, laser beams include a technical contradiction in which the intensity thereof should be high and low at the same time in consideration of the treatment effect and the stability. In this embodiment of the present invention, in order to overcome such a technical contradiction, the intensity of the main laser beam is set to be different from that of the auxiliary layer beams, and a basic intensity at the focus area is secured through the main laser element.

For reference, as the wavelength is small, the directness becomes strong. Therefore, the wavelength has an effect upon the penetration depth. The wavelength of the auxiliary laser beam having an intensity of 1 W may be set to 830 nm, and the wavelength of the main laser beam having an intensity of 5 W may be set to 808 nm. Such numerical values are only examples which were obtained while the present inventor was designing the present invention. Therefore, the wavelengths of the laser beams are not limited to such numerical values. Furthermore, a main parameter of the penetration depth is the intensity (power). That is, the main laser beam and the auxiliary laser beam may have the same wavelength.

The above-described embodiment of the present invention may be applied to TRIZ which is a problem solving principle. That is, the embodiment of the present invention includes a segmentation principle in which laser beams are segmented into the main laser beam and the auxiliary laser beams, a local quality principle in which the intensity of the main laser beam is set to be different from that of the auxiliary laser beams, a dynamicity principle in which the irradiation angle of the auxiliary laser beams is adjusted, and a preliminary action principle in which the auxiliary laser beams are used to activate the surrounding tissues. In addition, a principle of changing color is applied to the embodiment of the present invention. This will be described below through the color adjustment unit 140.

The color adjustment unit 140 described with reference to FIG. 1 serves to irradiates a color, of which the color is adjusted by controlling the intensities of red light and blue light, onto the skin of an affected area. Referring to FIG. 5, the color adjustment unit 140 is provided in through-holes 102c of the support member 102, similar to the main laser unit 110 and the auxiliary laser unit 120. In order to implement the color adjustment unit 140, at least one pair of red light emitting diode 142a and blue light emitting diode 142b is required as illustrated in FIG. 14.

Figure 14:
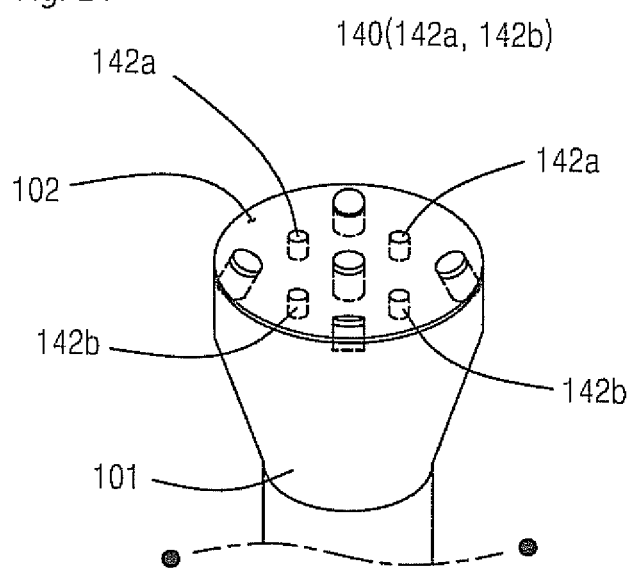
FIG. 14 is a diagram illustrating the detailed structure of the color adjustment unit in accordance with the embodiment of the present invention.

FIG. 14 illustrates two pairs of light emitting diodes as an example. Furthermore, FIG. 14 illustrates that the red light emitting diode 142a and the blue light emitting diode 142b are installed separately from each other on the support member 102. However, this is only an example. For example, the red and blue light emitting diodes may be formed in a package type. In other words, the red and blue light emitting diodes may be provided within a single package.

When the intensities of the light emitting diodes 142a and 142b are adjusted (color concentration adjustment), a variety of colors may be created by the color mixing principle. The mixed color is irradiated onto the skin of an affected area, and the absorption rates of the main laser beam and the auxiliary laser beam may be adjusted by the concentration of the mixed color. As the concentration of the mixed color increases, the absorption rate of the laser beams at the skin increases. At this time, the mixed color and the concentration thereof may be considered according to the skin color.

Meanwhile, the control unit 150 serves to control the operations of the main laser unit, the auxiliary laser units, the angle adjustment unit, and the color adjustment unit. Furthermore, the control unit 150 includes a function of supplying and controlling power required for the operations.

Figure 15:
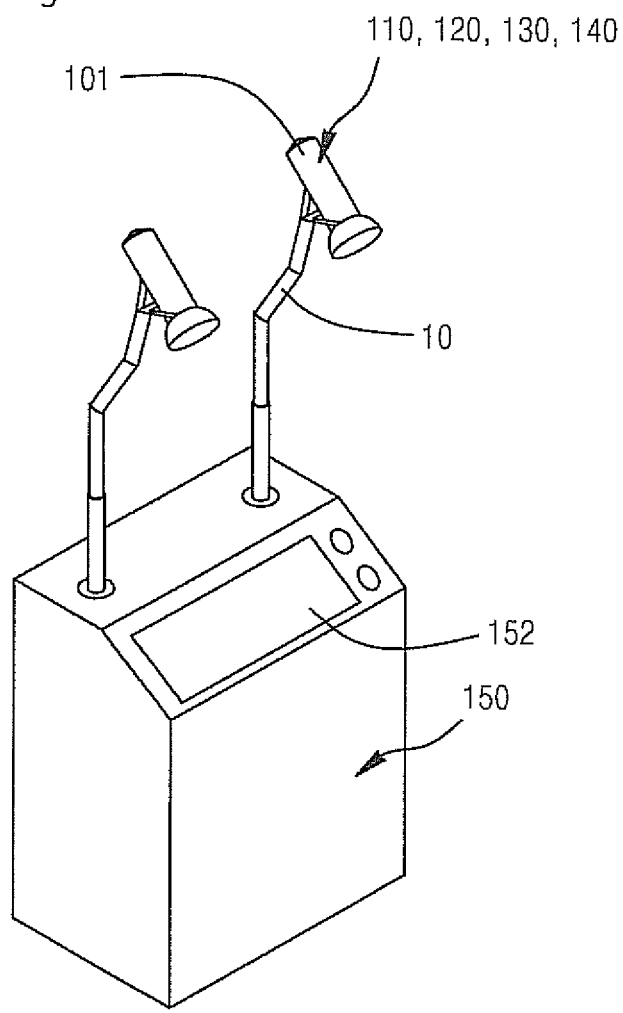
FIG. 15 is a diagram illustrating a modification of the present invention.

The above descriptions of the medical treatment apparatus 100 in accordance with the embodiment of the present invention have been focused on the functions thereof. The detailed structure of the medial treatment apparatus 100 may be modified in various manners. For example, referring to FIG. 15, the control unit 150 may be implemented in an external type which is separated from the body 101 of the medical treatment apparatus 100. The body 101 may be supported by the control unit 150 through a separate support member 10, and a plurality of bodies 101 each including the respective components 110, 120, 130, and 140 may be provided and controlled by the single control unit 150 as illustrated in FIG. 15. That is, a mono-bi-poly principle may be applied, if necessary.

Figure 16:
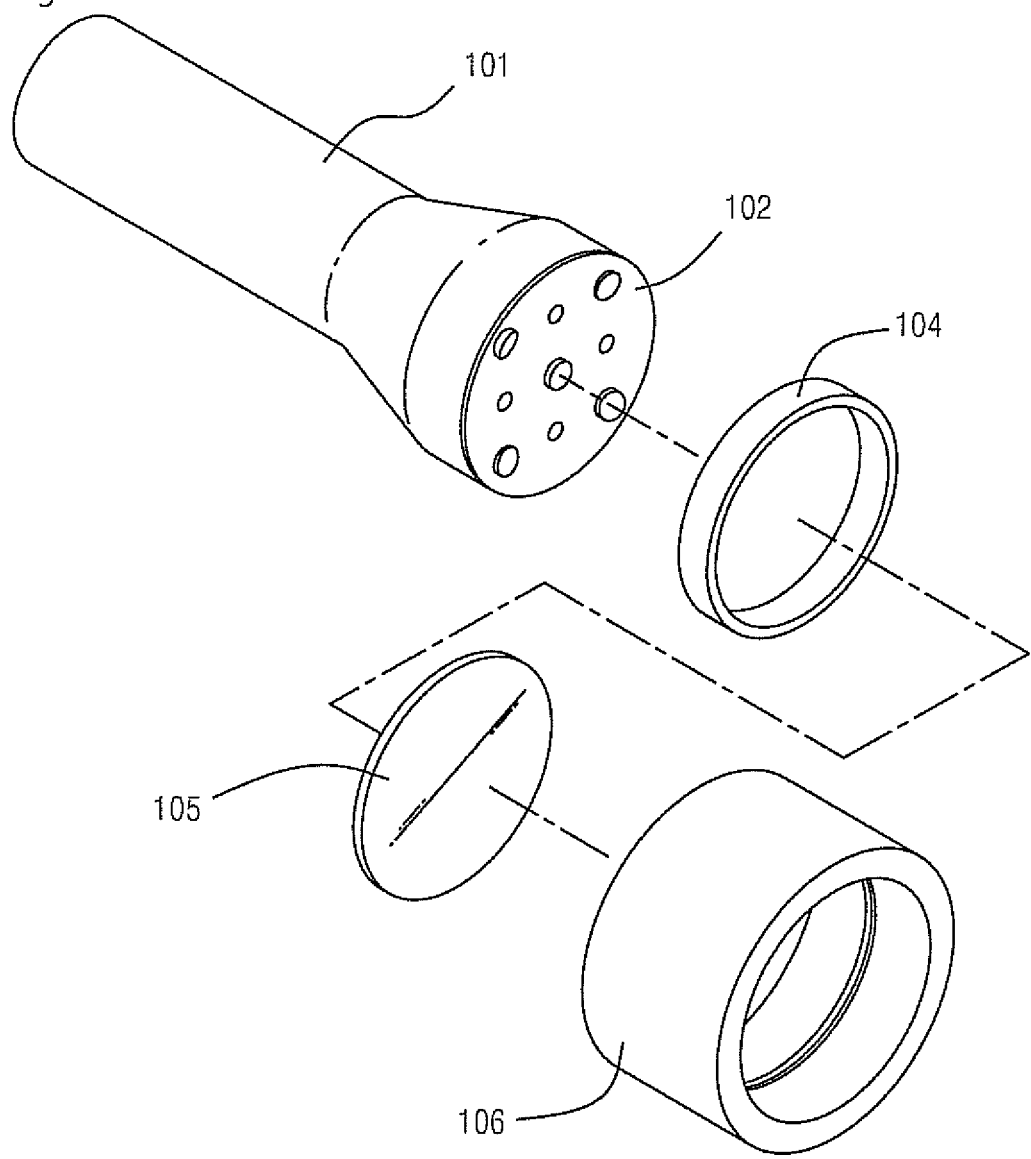
FIGS. 16 and 17 are diagrams illustrating additional components in accordance with the embodiment of the present invention.
Figure 17:
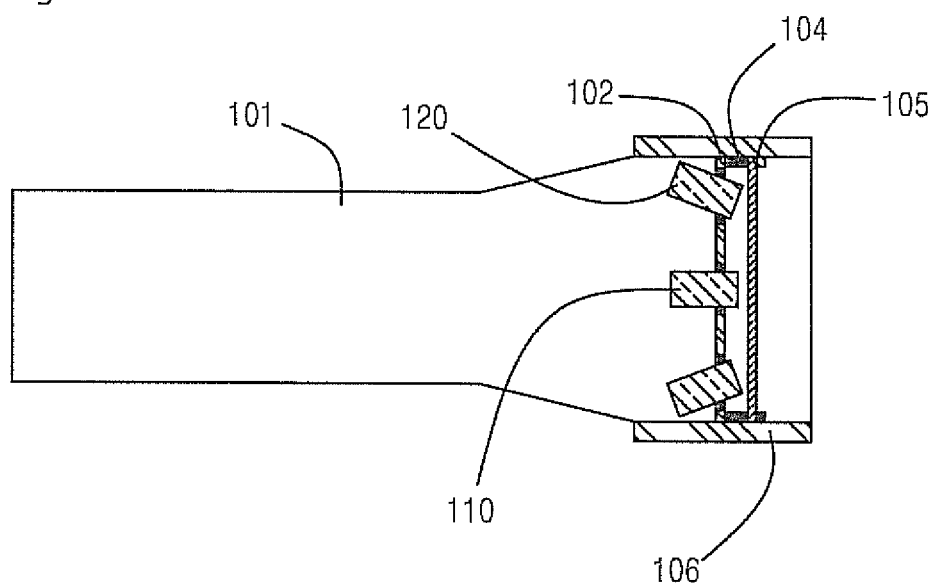
Figure 18:
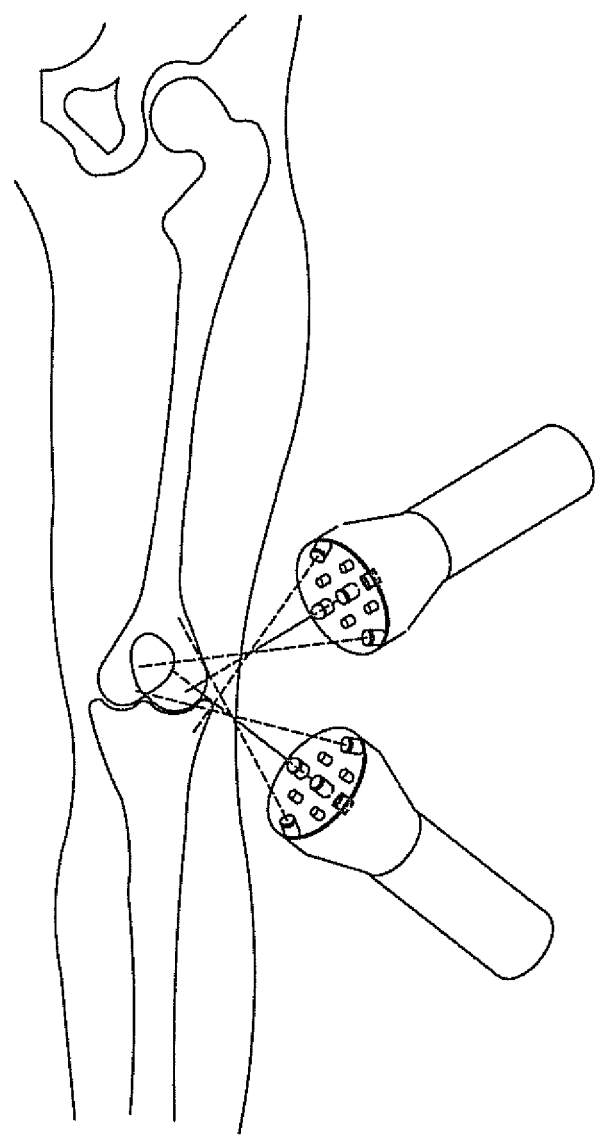
FIG. 18 is a diagram illustrating a state in which a joint is treated by the medical treatment apparatus using laser beams in accordance with the embodiment of the present invention.

FIGS. 16 and 17 are diagrams illustrating additional components provided in the medical treatment apparatus 100. The medical treatment apparatus 100 additionally includes a spacer positioned at the front surface of the support member 102, a transparent protection member 105 positioned at the front surface of the spacer 102, and a cylindrical coupling member 106 for coupling the spacer 104 and the transparent protection member 105 to the body 101. FIG. 18 conceptually illustrates a state in which a joint is treated by the medical treatment apparatus 100 using laser beams.

In accordance with the embodiment of the present invention, the focus of the laser beams may be easily changed, a treatment effect may be enhanced by the laser beams having different intensities, and the absorption rates of the laser beams may be controlled based on the color of light which is separately irradiated onto the skin of an affected area.

While the present invention has been described with respect to the specific embodiments, it will be apparent to those skilled in the art that various changes and modifications may be made without departing from the spirit and scope of the invention as defined in the following claims.

What is claimed is:

1. A medical treatment apparatus, comprising:
   a body;
   a main laser unit, associated with the body, to irradiate a near infrared (IR) main laser beam in a direction perpendicular to a target area;
   a plurality of auxiliary laser units, associated with the body, to irradiate near IR auxiliary laser beams to intersect a central axis of the near IR main laser beam at a focal distance;
   an angle adjustment unit, associated with the body, to adjust the focal distance by rotating the plurality of auxiliary laser units; and
   a color adjustment unit, positioned at a front surface of the body, to irradiate variable intensity red light and blue light on the target area.

2. The medical treatment apparatus of claim 1, wherein the near IR auxiliary laser beams have a lower intensity than an intensity of the near IR main laser beam.

3. The medical treatment apparatus of claim 1, wherein the main laser unit is positioned at a center of a front surface of the body.

4. The medical treatment apparatus of claim 3, wherein the plurality of auxiliary laser units are radially positioned, at a front surface of the body, around the main laser unit.

5. The medical treatment apparatus of claim 4, wherein the main laser unit comprises:
   a main laser element to irradiate the near IR main laser beam; and
   a condensing lens to condense the near IR main laser beam.

6. The medical treatment apparatus of claim 5, wherein the plurality of auxiliary laser units comprises four auxiliary laser units, and wherein each auxiliary laser unit comprises:
   an auxiliary laser element to irradiate an auxiliary laser beam; and
   a condensing lens to condense the auxiliary laser beam.

7. The medical treatment apparatus of claim 1, wherein the color adjustment unit comprises:
   at least one pair of red light emitting diodes and at least one pair of blue light emitting diodes.

8. The medical treatment apparatus of claim 1, further comprising:
   a control unit to control the main laser unit, the plurality of auxiliary laser units, color adjustment unit, and the angle adjustment unit.

* * * * *